United States Patent [19]

Charles et al.

[11] Patent Number: 4,628,737

[45] Date of Patent: Dec. 16, 1986

[54] METHOD AND DEVICE FOR LOCATING AND CHARACTERIZING FLAWS IN A KNOWN, SUBMERGED METAL STRUCTURE

[76] Inventors: Joël Charles, 27, Boulevard Grignan, 83100 Toulon; Lionel Gaudriot, Le Bourg, 69300 Lozanne; Jean-Marc Parot, 30, Chemin de la Ronde, 69160 Tassin la Demi Lune, all of France

[21] Appl. No.: 694,989

[22] Filed: Jan. 25, 1985

[30] Foreign Application Priority Data

Jan. 26, 1984 [FR] France .................. 84 01426

[51] Int. Cl.⁴ ............................................. G01N 29/04
[52] U.S. Cl. ........................................................ 73/624
[58] Field of Search .............. 73/624, 606, 607, 620, 73/625, 626, 627, 628, 629, 641, 602, 594; 367/7, 11, 87, 99, 100, 117, 131

[56] References Cited

U.S. PATENT DOCUMENTS

| | | | |
|---|---|---|---|
| 3,426,585 | 2/1969 | Zemanek, Jr. et al. | 73/622 |
| 4,001,764 | 1/1977 | Holland et al. | 73/40.5 A |
| 4,102,203 | 7/1978 | Sylvester et al. | 73/620 |
| 4,128,011 | 12/1978 | Savage | 73/594 |
| 4,481,818 | 11/1984 | Hellquist | 73/587 |

FOREIGN PATENT DOCUMENTS 1422556 1/1976 United Kingdom .

OTHER PUBLICATIONS

H. Crohas et al., *Oil & Gas Journal*, Damage-Detection Monitoring Method for Offshore Platforms is Field-Tested, vol. 80, No. 8, Feb. 1982, pp. 94, 99, 100 and 103.

*Primary Examiner*—Stephen A. Kreitman

[57] ABSTRACT

The ultrasonic pulse-echo method for locating and characterizing flaws in a partly submerged metal structure utilizes a device comprising an acoustic antenna (3), means (18) for preprocessing the echo signals, data transmission means (23–23') and a central processing unit (6).

11 Claims, 10 Drawing Figures

METHOD AND DEVICE FOR LOCATING AND CHARACTERIZING FLAWS IN A KNOWN, SUBMERGED METAL STRUCTURE

This invention relates to the general technical field of submerged structures and specifically concerns the problem of locating and characterizing any flaws which might occur in all or part of the constructional elements of such a structure.

The invention concerns submerged metal structures having a known geometrical configuration, such as a plane structure, a caisson or, more to the point of the invention, a truss.

Submerged metal structures, regardless of their specific shape, require frequent inspection for flaws or damages affecting their structural integrity. Such inspections are designed to assess the importance of any changes which may have occurred in the mechanical strength characteristics of the structure and determine whether the safety requirements for the structure are still being met.

Given the poor visibility usually obtaining in the liquid environment surrounding the structures and the latter's large size and complexity, such inspections are carried out by human divers equipped with suitable diving gear. Localized field inspections of this type, involving non-destructive testing, entail that the surfaces to be inspected first be suitably cleaned and require that some means of fault detection be carried to the point of inspection and applied thereto, said means usually involving optical, vibratory or ultrasonic devices.

Obviously, such methods are not easily implemented, inasmuch as the area covered is always very small. Moreover, the preliminary cleaning of the surfaces to be inspected often proves difficult. And the diver is required to move, sometimes at great depths, about a structure which he is at some pains to suitably evaluate and within which he faces major difficulties of orientation due to the short range of visibility in a marine environment.

It is thus virtually impossible to carry out a reliable overall survey of a truss-type structure under the above-mentioned conditions. Furthermore, such inspections are costly and in some cases risky for the personnel involved, particularly since the annual time allotment therefor is sometimes extremely limited, as in the case for example of North Sea operations.

Another proposed method has been to plant acoustic sensors near the most-stressed parts of the structure. Such an approach however does not enable comprehensive inspection of a marine structure at reasonable cost.

Still another approach proposed would consist in using conduction electrodes designed to electrically monitor the field of a sealed chamber installed near the welds at junctions of the structural members where water might penetrate as the result of cracking. Such a technique is also unreasonably costly and necessarily requires means for checking the operation of the electrodes if the reliability of the results is to be trusted at all.

Yet another proposed solution has been to pressurize the tubular members of a truss, either individually or in groups, and then to monitor them for pressure leaks which would reveal a through-crack. Such an approach, equally costly and difficult to implement, cannot be envisaged for an entire submerged structure and furthermore allows only those flaws involving a through-crack of the concerned surface to be detected.

A vibration technique has also been envisaged, to analyze the dynamic responses to overall stresses from sea swell or to localized stresses induced by suitable means. The processing of the results obtained by such a technique is especially complex in the context of a truss framework and the results obtained with regard to the structure's natural resonance have not proved sufficiently sensitive to the relatively small flaws one wishes to detect and locate.

The invention is directed to overcoming the above-mentioned drawbacks by proposing a new method and a new device for fault location and characterization, particularly for flaws of a decimetric order, occurring in a known type of submerged metal structure, which may be implemented without the need to implant any localized technical devices and not requiring divers or diving machines that would have to be stabilized and oriented in precise spatial directions in relation to a given structure under test.

Another object of the invention is to provide a new structural monitoring technique being substantially less costly to implement than the prior art techniques, yet capable of supplying reliable overall or localized measurements of any given structure.

Yet another object of the invention is to provide a flaw search and characterization technique enabling an operator to proceed directly with the location and characterization of possible faults from a remote control console.

Still another object of the invention is to provide a fast and accurate technique of fault location and characterization able to be implemented from the surface and without the need for even partial preliminary cleaning of the portion of the structure to be inspected.

Yet still another object of the invention is to provide a fault location and characterization technique applicable to a broad field, up to the decametric scale, such that an entire, known submerged structure can be inspected comprehensively in a reasonable time span—something which can be deemed extremely difficult, if not impossible, to achieve with the prior art techniques, at least for some types of submerged offshore structures.

A still further object of the invention is to provide a fault location and characterization technique that can be easily implemented in the midst of a truss framework whilst at the same time solving the problem of localizing the detection means involved in relation to the structure to be explored.

To meet the above-stated objectives the method or technique according to the invention consists in:
placing a sound transmitting and receiving probe or antenna having a plurality of receiving transducers within acoustic range of the structure;
emitting at least one ultrasonic acoustic pulse at a frequency in the 30 to 150kHz range;
picking up echo signals from n specular reflection points of the structure, or highlights;
determining the angular coordinates of the reflection points by determining the sequence in which the series of pulse echoes are received and classifying the first-in-time echo signal received from each point by one of the receiving transducers, followed by the series of delayed echo signals associated therewith and picked up by the other transducers;
determining the theoretical coordinates of the various highlights;

determining the position of the antenna, on the basis of the latter coordinates;
displaying the pattern of highlights;
comparing this pattern with the stored theoretical image of the structural part being inspected;
and revealing, by comparison, the presence or absence of any new reflection points with respect to the theoretical highlights or isotropic points of the structure.

The invention also provides a device for the location and characterization of flaws, said device consisting of:
an acoustic antenna comprising
  means of relatively fixedly supporting said antenna in the liquid medium,
  an acoustic pulse transmitter,
  and a receiving surface made up of x vibration-sensitive cells;
means for preprocessing the echo signals, comprising, for each sensor cell,
  at least one preamplifier,
  a filter associated with a logical comparison and decision module for determining the presence of a signal,
  and a filtered signal addressing and labelling module;
a data transmission means for the above data;
and a central processing unit, including
  a computer,
  display means,
  and comparison and storage means.

Various other features and advantages of the invention will become apparent from the following detailed description with reference to the accompanying drawings which illustrate one non-limiting example of an embodiment of the invention and wherein.

Figure 1:
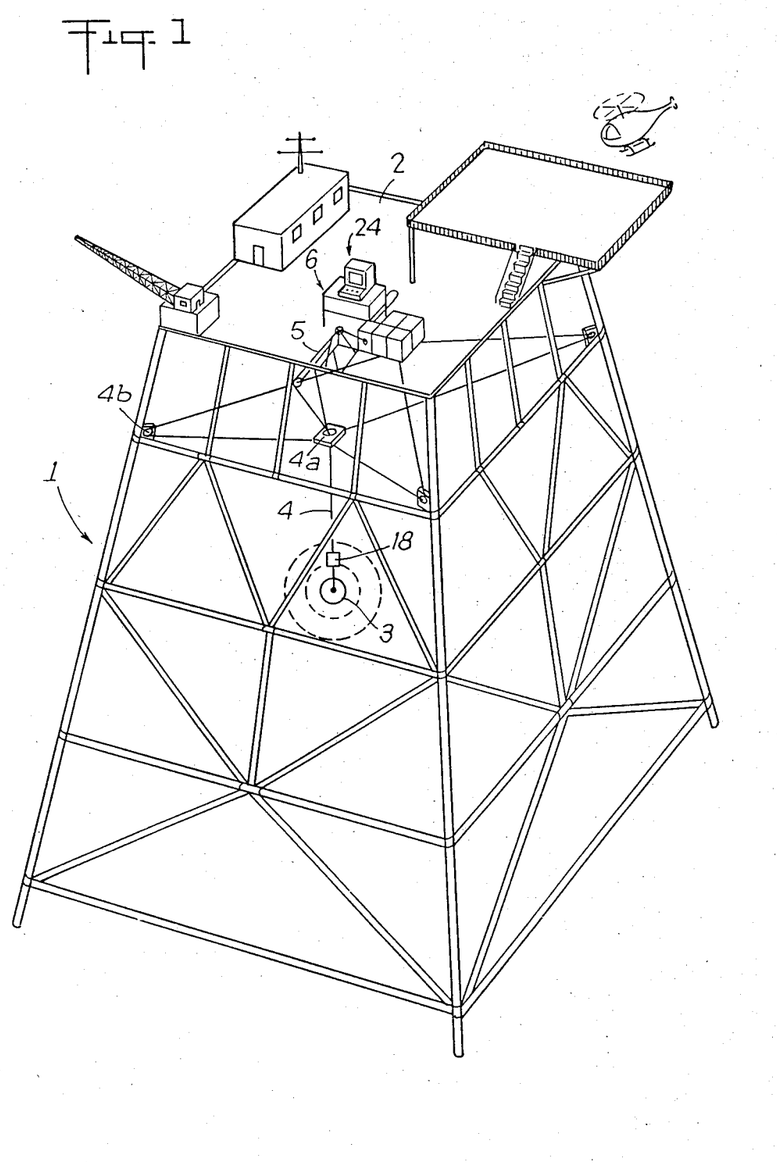
FIG. 1 is a schematic drawing in perspective illustrating the implementation of the method and device according to the invention.

Referring now to FIG. 1, a submerged structure 1 is shown, being for example a truss of tubular members supporting a platform 2 above water level, or topside platform affording an access or working area.

The embodiment illustrated is given merely by way of example, for the invention can be used to locate and characterize defects in other structures than a metal truss structure. For example, it can be applied to the inspection, location and characterization of flaws in a metal structure in the form of a wall or caisson (pile).

Structures of the above-mentioned type must be carefully scanned and inspected in order to detect not only the maintenance of their mechanical integrity but also the possible appearance of defects with a potential, depending upon their change over time, of adversely affecting the structures' overall safety.

The problem raised is therefore one of being able to carry out a rapid and comprehensive inspection of a structure of any type, capable of conveniently and reliably yielding a definition or characterization of any flaws found thereby to enable immediate assessment of the consequences likely to result therefrom or the evolution of the flaws over time.

The subject invention is directed to solving this problem.

As shown in FIG. 1, the invention consists in installing a first means, consisting of an acoustic probe 3 made up of sound transmission and reception transducers arranged in the form of two concentric spherical surfaces.

Said probe 3 is suspended from a cable 4 operable to be reeled in or unreeled from a suitable reeling device 5 installed on the platform 2. The cable 4 plays the dual role of suspending the antenna physically and protecting the technical means used to remotely transmit commands to and scanning results from the probe.

In one specific embodiment of the invention said cable 4 moreover runs through a slip cage 4a which can be moved by means of a system of slinging cables running through idler pulleys 4b installed in the corners of the horizontal field of the structure to be scanned, the length of said slinging cables being adjustable by separatelyacting winches. This system, or any other suitable adjusting means, enables the operator to horizontally position the probe within the defined field and thus to bring it closer to the members of the structure on which he wishes to focus his inspection.

In the case of an application to a structure having another shape than the one illustrated, the cable 4 could be replaced by a stiff suspending member such as a bar or rod associated, via vertical means, with a carrying cage operable to be moved along a horizontal path.

The probe 3 is designed to emit ultrasonic pulses within a frequency range of 30kHz to 150kHz in order to collect the echoes produced by reflection and backscattering from the structural members, in view of obtaining data for processing by a computation unit 6 included in the control console on the platform 2.

Alternatively, the probe 3 could be carried by a submarine apparatus, whether self-powered or not, transporting the operator and his control console, or linked to the latter via an umbilical carrying the signals picked up by the probe 3.

Figure 2:
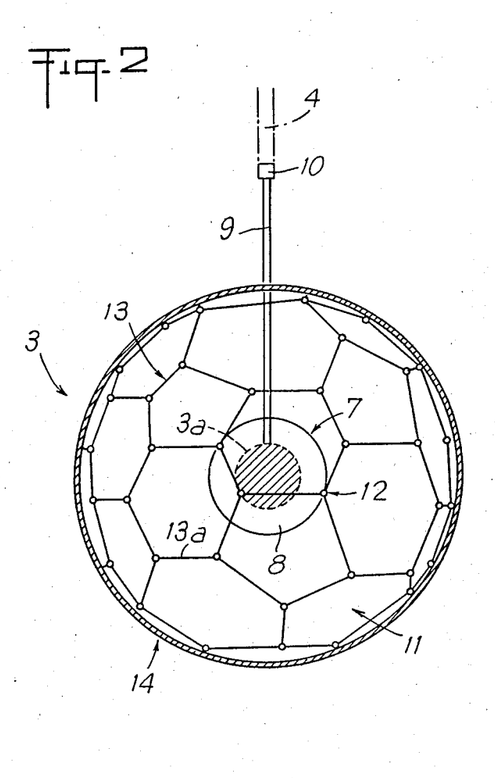
FIG. 2 is an elevation, on a larger scale, of one of the components of the invention, namely of item 3 of FIG. 1.

In the context of the preferred embodiment illustrated by the accompanying drawings, the probe 3, as depicted in FIG. 2, consists of a spherical transmitter 7 comprised of evenly spaced, identical transducers, all oriented radially and enclosed in a spherical protective shell which can be made of metal or of a composite material. The transducers are physically connected to the shell 8, which acts as a radiant surface, generating a regular spherical wave whenever the transducers are simultaneously excited. The center of shell 8 establishes the acoustic center for transmissions and the shell 8 itself is attached to a tubular adapter 9 having a fitting 10 for hookup to cable 4. The adapter 9 further serves to support and protect at least one conductor designed to supply the transducers with the energy required to produce excitation, said excitation generally being provided in the form of a discharge from a suitable condensor in a generator 3a which can preferably be located in the core of the antenna.

The probe 3 further comprises a spherical receiving surface 11, built concentrically around the spherical ultrasonic source or transmitter 7 which it envelopes. Said receiving surface 11 is made up of x sensitive cells 12 or receiving transducers individually supported by an acoustically transparent structure 13.

For example, said receiving transducers 12 can be mounted according to a radical orientation, at the nodes of the peripheral structure 13 which may be a steel lattice or any other frame material. Such a lattice frame is preferably made up of segments 13a forming the edges of a regular polyhedron. According to a preferred embodiment, said structure 13 can bound an envelope defining, on the basis of ninety segments 13a, thirty-two pentagonal or hexagonal plane surfaces joined together by sixty nodes or points having the said transducers 12 mounted thereon.

Said transducers 12 are connected to conductors carried and protected by the adapter 9 to which the lattice framework 13 is attached in such a manner as to be arranged perfectly concentrically about the spherical transmitter 7.

As shown in FIG. 2, the receiving surface 11 can be enclosed in a protective shell 14 made of an acoustically transparent material. Said shell 14 can for example be made of a composite material.

The conductors leaving transducers 12 are routed to a preprocessing unit 18 preferably located in a watertight container attached to cable 4.

This pre-processing unit 18 receives the signals coming from all the receiving transducers 12, preamplifies each of the signals, effects a preliminary filtering and identification or said signals and transfers the resulting logical data to the processing unit 6 via the signal cable contained in suspension means or cable 4.

Figure 3:
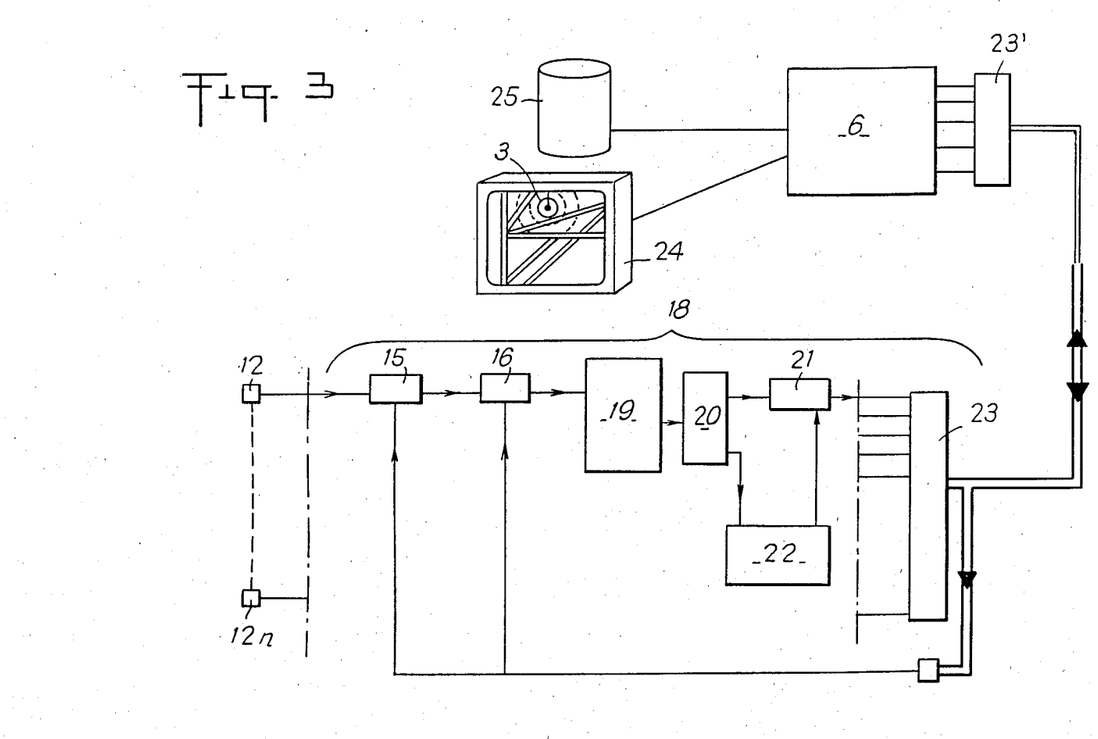
FIG. 3 is a schematic drawing of part of the means used in the invention.

According to a preferred embodiment of the invention, as depicted in FIG. 3, said pre-processing unit 18 comprises one preamplifier 15, one programmable gain devicd 16 and one adjustable filter 19 for each receiving transducer 12.

The next component of the signal pre-processing unit 18, ie. item 20 of FIG. 3, carries out the logical decision as to the detection of a useful signal and correlatively sends a code to a buffer register 21 which, besides, receives from a tagging module 22 any useful data serving to identify the signal thus detected, such as the number of the receiving channel and the effective acquisition time.

The set of data from register 21 then goes through a digital multiplexor 23 for sending in serial mode over a coaxial link in suspension cable 4 to processing unit 6 on the platform 2, after demutiplexing in a demultiplexor 23'.

The processing unit 6 processes the signals sent by pre-processing unit 18 in order to spatially localize the probe within the structure, to reconstitute the geometry of the local portion of the structure being examined by comparison with the initial data of the stored engineering drawings and to show up, initially, by observation of a lacking echo where there should be an echo related to a highlight or inherent isotropic point of the structure, any outright break-off of a structural member whereof the echo is found lacking.

Processing unit 6 is accordingly associated with three-dimensional graphic display means 24 enabling the operator to see the geometry of the structure in the vicinity of the probe, to locate the probe in this perpsective view and to locate the highlights corresponding to the echoes having been detected. Said unit 16, for this procedure, relies on a mass storage 25 containing in particular the characteristics of the truss making up the structure and any other physical data available from the engineering drawings.

The means of the invention described above come into play as follows.

Figure 4:
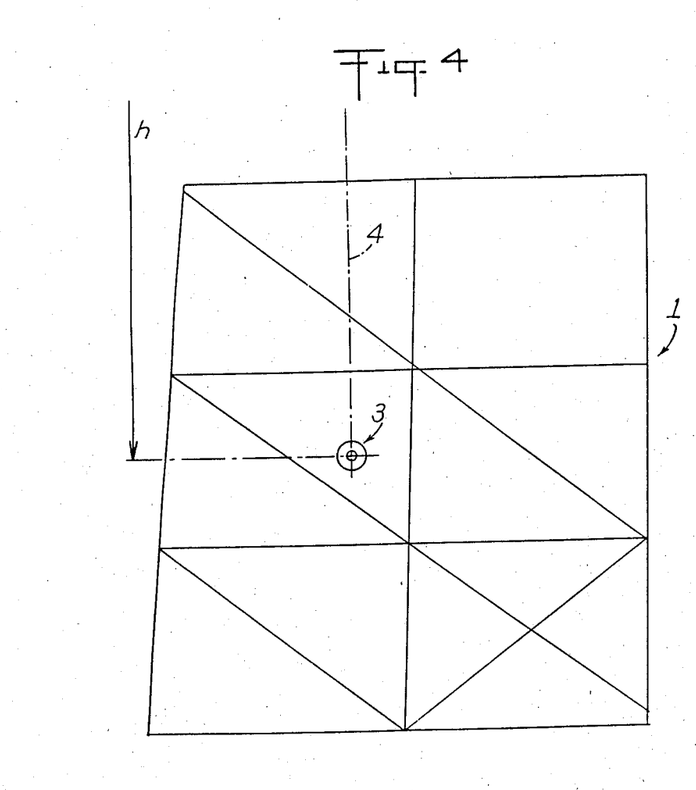
FIG. 4 is a schematic drawing illustrating a first step in the implementation of the invention within a metal structure.

The probe 3 is immersed inside the structure 1 being inspected and within acoustic range of the structure by means of reeling device 5 which maintains it at a given depth or level h and in a relatively stable, specified horizontal position as depicted in FIG. 4. Generator 3a is then powered so as to supply the transducers of spherical transmitter 7 with the energy required for their excitation in view of setting up the ultrasonic pulsation generating a smooth spherical wave. For this purpose said transmitting transducers of sphere 7 can be powered by the discharging of a capacitor through pulse shaping circuits such as to deliver a modulated wave train in the 30 to 150kHz frequency range with a duration of the order of 50 μs.

The structural members located within acoustical range of the probe 3 react, on receiving this acoustic pulse, by generating a return radiation in the direction of probe 3. The set of echoes produced by said structural members thus pass through receiving surface 11 which is acoustically transparent.

All of the transducers 12 are thus influenced by each of the echo signals, which is then preamplified by preamplifier 15 and software gain-controlled by component 16. Each signal is the filtered by pre-processing unit 19 and sent, after encoding, to buffer register 21 following validation and tagging by module 22.

Figure 5:
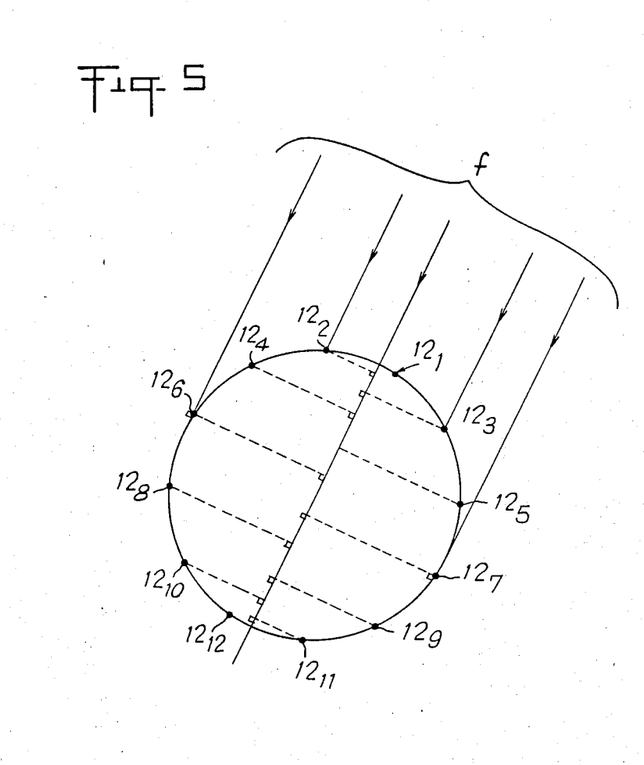
FIG. 5 is a schematic drawing illustrating another step in the implementation of the invention.

Considering a back-reflected beam f returning to spherical receiver 3, as illustrated in FIG. 5, it is obvious that the echo will first impinge on a first transducer 12 associated with the ray covering the shortest distance. The same echo signal will then impinge successively on the various other transducers, except with a time lag in reaching each transducer corresponding to the relative distances to be covered by the different rays. This fact is illustrated in FIG. 5, in which example only the rays and transducers located in one diametrical plane of the sphere are represented for purposes of clarity. According to this representation, the subscripts added to reference 12 stand for the order in time of preception of the echo signal by the various transducers.

Obviously, the same applies for any and all beams of back-reflected rays regardless of their direction of origin and their degree of parallelism or divergence.

All the echo signals encoded as above go through the multiplexor 21 and are then transmitted serially over a coaxial line in cable 4, to the topside computer 6 after going through demultiplexor 23'.

The first step in the automatic operation of the method according to the invention consists in detecting the echoes from the highlights for purposes of localizing the probe.

The computer 6, which has stored all the coded echo signals, looks up in its store the first-in-time received echo signal which also corresponds to the point of interaction with the nearest structural element. By reading the identification code, the computer can determine the position on the sphere of the concerned transducer 12 and, consequently, can find the approximate orientation of the back-reflected beam producing the echo.

The computer 6 is programmed to compute the likely ranges of times in which a given echo wavefront having been sensed by a first transducer 12 will subsequently be perceived by the succeeding transducers on surface 11. The signals thus sorted, thus constitute a timed sequence associated with a given echo beam. The computer 6 seeks to build this sequence and thus gradually pinpoints the orientation of the back-reflected beam.

When the first sequence, corresponding to the first wavefront, is constructed, the computer 6 begins to build the (sometimes interleaved) sequence corresponding to the next-detected back-reflected wavefronts.

Based on the data acquired in this way, computer 6 first determines the spherical coordinates of each bright spot in relation to the center of the antenna, in a coordinate system related to the probe. Based on the stored geometrical data about the structure's design, it computes the probe's position and orientation in the structure's coordinate system.

The data are processed by integrating the measurement of the antenna's depth (level of immersion), in order to clear up any ambiguity of estimation that might arise in the case of a submerged structure built up from repetitive modular units.

The means of the invention as described in the foregoing, accordingly enable accurate localization of the probe within the structure in a very short amount of time and using very compact hardware.

Figure 6:
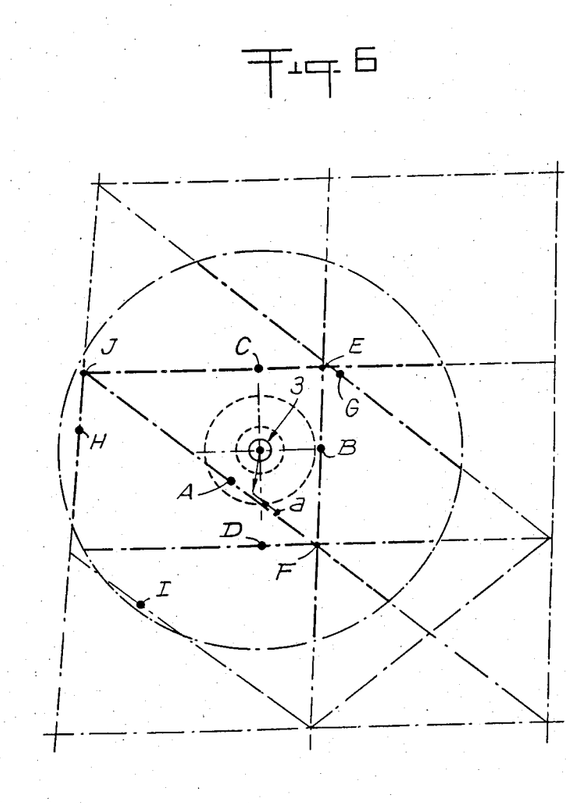
FIG. 6 is an elevation illustrating a characterization scan in a truss related to FIG. 4.

The second step of this first phase of processing consists in displaying on display means 24 all the bright spots which have been computed in order to subsequently join them and reveal the local construction of the structure as it "appears" to the antenna 3. FIG. 6 shows, by way of example, the diagram which can be obtained with the help of means 24. The bright spot nearest the antenna in this diagram is labelled A and the successive more distant spots are respectively labelled with the following letters of the alphabet, the furthest point in the given acoustic range designated by the letter J.

This diagram is then compared with the local geometric image (FIG. 4) stored in memory 25. This comparison makes it apparent that the echo points correspond to acoustic highlights A, B, C, D, G, H, I and to isotropic points E, F and J. However, should this comparison reveal an echo point a not belonging to either of the above categories, such a point, given its position, can only be a back-reflection source on a specific, identifiable member of the structure. Such a can only be interpreted as a manifest, unexpected irregularity in the structure, possibly due to a clear defect such as the cracking of a brace or strut for example.

The foregoing example does not fully elucidate the inspection capabilities of the invention. Conversely, the lack of an echo point at a location where at least one should show up reveals the disappearance of a structural member.

The first phase of the technique then, initially provides an overall evaluation of the structure's mechanical integrity and a characterization of the most pronounced flaws by comparison between the inspection diagram, such as that of FIG. 6, and the computer's stored engineering drawing of the local area concerned, such as that of FIG. 4.

Obviously however, one will in many cases not wish to be limited to such a general evaluation of structural integrity. It will often also be important to be able to systematically detect lesser structural defects, such as cracks, which might later, if ignored or neglected, lead to outright breakage of the affected member.

The method according to the invention also provides, in a second phase or stage, for the detection of the last-mentioned type of flaws, based on the physical properties of Lamb waves.

As a rule, an acoustic ray corresponding to a bright spot struck by a perpendicular ray is totally reflected.

On the other hand, reflection is only partial for certain critical angles of incidence. In the case of a 30° incidence, the acoustic wave generates a zero-order antisymmetrical Lamb wave, with a substantial coupling effect, having a group velocity on the order of 3100 m/s for wave packs in the selected frequency band (30–150kHz) and wall thicknesses such as those of the structural members in common use in the offshore structures to be investigated.

Such a Lamb wave (FIG. 7), generated by an acoustic ray having an angle of incidence Ri, is characterized by a mechanical ray Rm, located in the plane Pl of the incident acoustic ray. Ray Rm brings about the re-emission of an acoustic wave characterized by rays Ri' symmetrical to incident ray Ri, resulting in an attenuation of ray Rm in its path.

Figure 7:
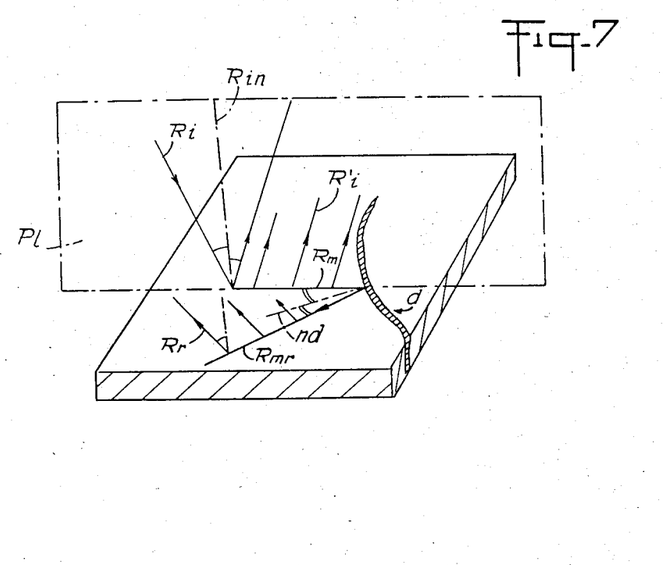
FIG. 7 is a partial perspective view illustrating how a physical property is seen by the invention.

The Lamb wave, and correlatively the mechanical ray Rm are reflected by any crack-type defect d found in their path, in a classic symmetrical pattern with respect to the perpendicular or normal line nd to the crack. The reflected mechanical ray Rmr brings about the emission of backscattered or reflected acoustical rays Rr which emerge reciprocally 30° from the perpencular to the structural member and which thus carry an echo signal characteristic of the crack's presence. In the case where the mechanical ray Rm is perpendicular to the crack, the traverse of the backscattered rays is the reverse of that of the incident rays and one of the backscattered rays Rr specifically coincides with Ri. These—the reverse rays and their neighbors—are the rays which are utilized in the second phase of the technique according to the invention, on the assumption that the creation of echoes through the intersection of a spherical incident beam with the structure is based on the following physical principles:

Given the wavelengths assocated with the acoustic signals being transmitted (30–150kHz frequency band) through both water and metal (wavelengths on the order of centimeters), the acoustic propagation effects in these two media may be described in terms of ray acoustics.

Given the beamwidth of the spherical receiving antenna (several tens of acoustic wavelengths), the structural elements or members nearest the probe will always be in the first Fresnel field of the antenna and consequently the directional pattern of this antenna will be in the form of a uniform beam of rays normal to be wavefronts, confined within the apparently circular contour of the antenna. This limited beamwidth characteristic is preserved for the same reasons in the beams generated in the metal structures.

Figure 8:
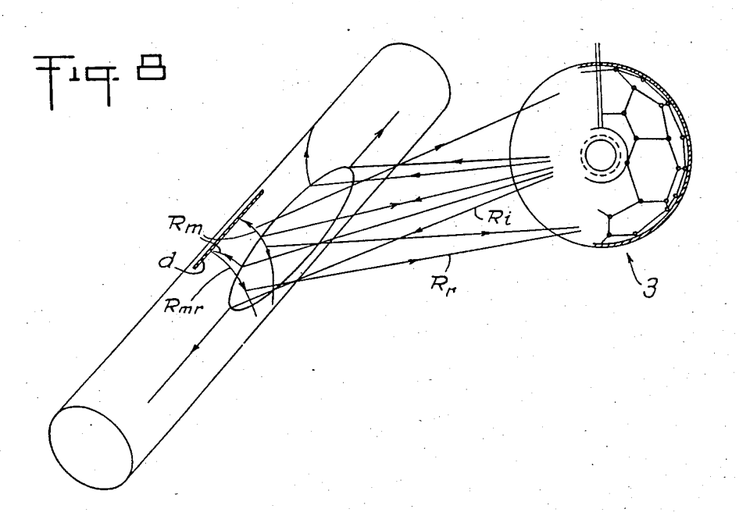
FIG. 8 diagrams the signal path of a reflection from a longitudinal defect in the context of the invention.
Figure 9:
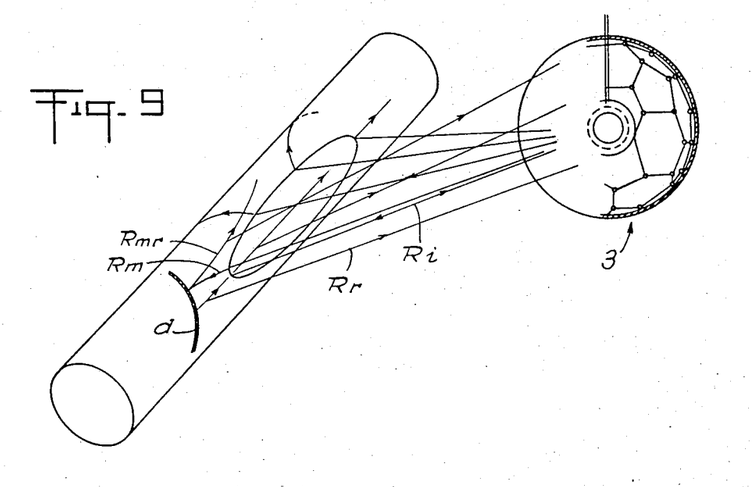
FIG. 9 diagrams the signal path of a reflection from a transverse defect.

The application of these basic physical principles to the detection of flaws based on the beams of rays emitted and received by the spherical probe is illustrated in the drawings in terms of the three different possible cases. FIG. 8 illustrates the case of a longitudinal crack; FIG. 9, the case of a transverse crack (i.e. in a cross-sectional plane of a chord); and FIG. 10, the case of an oblique crack. In these last three figures, like parts bear like references, taken from FIG. 7.

Figure 10:
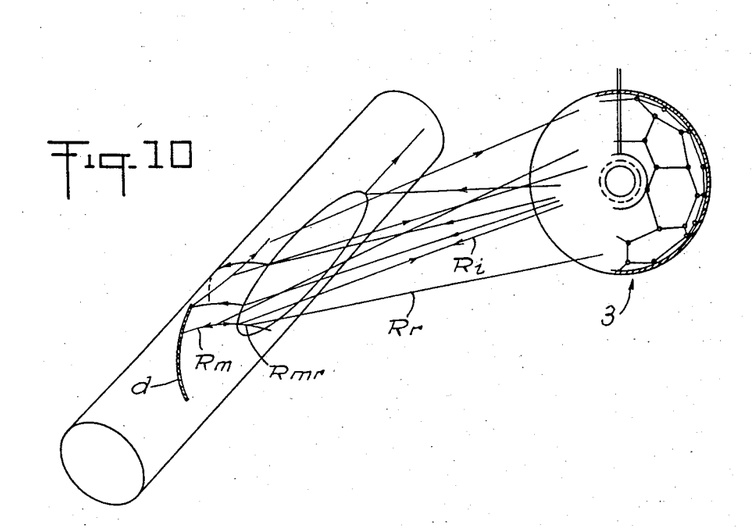
FIG. 10 diagrams the signal path of a reflection from an oblique defect.

The reflected beams represented in the figures, which carry the echoes emanating from the crack, are typical of the wavefronts that are sorted at reception by suitable processing of the received echo sequences associated therewith, for the purpose of concentrating the system's detection capabilities on the presumed flaws being sought.

This processing is carried out by the previously described circuits as follows:

In order to put the above-stated principles into practice, it is necessary to be able to electronically configure or "preconfigure" the receiving antenna 11 in such a manner as to enable the beam or bundle of acoustic rays coming from a predetermined portion of the structure or, more accurately, from a predetermined structural member, at an incidence of about 30°, to be selected for monitoring. Such preconfiguration of the scanning beam implies some kind of processing of the sequence of perceived echoes and the reconstitution of the corresponding wavefronts. The family of perpendiculars to these wavefronts defines the beam of refelected rays which will be backscattered through the water and the structural members in their path.

Several different procedures can be implemented for the purpose.

For example, the various transducers 12 can be associated with adjustable delay lines, in order to provide a relative time delay between them and thus make available a global perception of the echo signal carried by the wavefront having been selected after the first firing. Such means enables any radial scanning orientation to be selected and allows precise investigation of all or part of a structural element, once the probe 3 has been positioned and localized as described above.

In such a phase, any perceived echo resulting from the previously described "preconfiguration processing" will mean that a crack-type flaw is present in the scanned area, said flaw being localized in the metal as the locus of the intersections between the emitted incident rays and the received backscattered rays.

Conversely, the absence of an echo in this case can be deemed to indicate the absence of a flaw detectable by the resolution characteristics of the means according to the invention, meaning in the case at hand, the absence of a flaw oriented normally to the beam and having a transverse dimension smaller than the decimeter order.

It is also possible to utilize a preconfiguration synthesizing algorithm, resident in computer 6, enabling selection at the time of reception of the beams of backscattered acoustic rays which, when suitably imaged for the operator via display means 24, enable the operator to run the systematic search for defects.

Display means 24 in fact makes visible in the perspective of the structural area immediately surrounding the probe, the probe itself as well as both the forward and backscattered paths of the selected beam, and thus their field of intersection, which itself indicates a likely flaw area.

The preconfiguration synthesizing algorithm consists in:

picking the transducer whose radial direction corresponds to that having an angle of incidence of roughly 30° in relation to the structural area to be inspected;

estimating the mean global wavefront which is perpendicular to this direction, corresponding to an echo perceived by said first transducer and which must later be picked up in sequence by the other transducers in time slots defined by said estimate;

taking into account those echoes, among the one received and stored pursuant to a second acoustic emission, which fell in the predetermined time slots;

and analyzing the consistency of this sequence to decide about the presence or absence of a flaw.

In the event of an affirmative decision, it locates the flaw within the beam and displays it for the operator.

In this way, an operator can precisely scan the entire length and periphery of a structural unit forming part of a submerged structure merely by first selecting the successive observation points where the probe is to be located, moving the probe to the desired location with the help of its handling means and checking the horizontal position taken by the probe and correcting it as required.

It deserves to be pointed out that the second phase of the method according to the invention can involve a processing routine designed, especially in the case of estimating and making a likelinessbased search for an expected sequence of echoes, to utilize the data obtained following the first firing (made for purposes of locating the probe and checking structural integrity). In this case, the echo sequences are stored together with their identification data right after the first step.

The flaw detection procedure for crack-like flaws can run as follows:

The operator moves the probe about the structure with the help of the handling means to place it near the area to be scanned. The flaw detection method is based on the backscattering of mechanical waves bounced off the flaws. Said mechanical waves are induced in the structure by rays striking it at the most suitable incidence (FIGS. 4, 5 and 6).

The display means 24, controlled by computer 6, provides the operator with an image of the portion of the structure surrounding the probe, said image clearly showing, by means of a color scheme for example, the area being scanned in detail. Any flaws found at this point are also represented in the image.

The operator moves the probe in small increments in order to scan the entire structure, by operating the winch for vertical motion and means 4a for horizontal motion. The display means 24 images the area currently being scanned as well as all the previously scanned areas as viewed from all directions, since a flaw can only be detected when it is virtually perpendicular to the mechanical waves being propagated through the structure. The computer can also guide the operator in moving the probe about the structure to optimize the scanning process.

The invention should not be construed as being limited to the embodiment described, as various modifications will likely occur to those skilled in the art without departing from the scope of the following claims.

What is claimed is:

1. A method for locating and characterizing flaws in a known, submerged metal structure, said method consisting in:

placing a sound transmitting and receiving probe or antenna having a plurality of receiving transducers within acoustic range of a known, submerged metal structure;

emitting at least one ultrasonic pulse in the 30–150kHz frequency range;

picking up echo signals from n specular reflection points or highlights of the structure;

determining the angular coordinates of the reflection points by ordering the data concerning the arrival times of the various echoes at the sound probe's or antenna's various receiving transducers, according to various typical time sequences associated with wavefronts coming from n localized reflection points;

determining the theoretical coordinates of the various reflection points or highlights;

determining the position of said sound probe or antenna based upon said coordinate data;

displaying the pattern of said highlights;

comparing said pattern with the stored theoretical image of the structural area being inspected;

and revealing any lacking or additional reflection points compared with the structure's theoretical highlights or isotropic points.

2. Method according to claim 1, whereby said probe's receiving antenna is furthermore preconfigured to steer the scan in the direction of a specific area of the structure being inspected, such as to receive, after a second firing, the acoustic rays backscattered by a flaw and corresponding to a Lamb wave generated in the relevant structural member by an incident acoustic radiation with an angle of incidence of approximately 30°.

3. Method according to claim 2, whereby scanning is carried out by an acoustic antenna with a concentric spherical transmitting and receiving pattern.

4. Method according to claim 1, whereby the emitted pulse is given a duration of between 30 and 100 microseconds.

5. Method according to claim 3, whereby the receiving antenna is oriented toward the area of the structure to be scanned, using adjustable delay lines for the various transducers.

6. Method according to claim 3, whereby said receiving antenna is preconfigured by:

picking the transducer whose radial direction corresponds to that having an angle of incidence of roughly 30° with the structural area to be scanned;

estimating the mean global wavefront which is perpendicular to this direction, corresponding to an echo perceived by said first transducer and which must later be picked up in sequence by the other transducers in time slots defined by said estimating step;

taking into account those echoes, among all the ones received and stored pursuant to a second acoustic emission, which fall into the predetermined time slots;

and analyzing the consistency of timed echo sequence to decide about the presence or absence of a flaw.

7. Method according to claims 5 or 6, whereby the scanning direction of the receiving antenna is displayed in relation to an image of the local area of the structure to be analyzed.

8. Method according to claims 5 or 6, whereby said receiving antenna is directionally orientated following the emission of a localizing and structural integrity scanning pulse, whereafter the whole set of received and stored echoes is utilized in scanning for backscattered acoustic rays corresponding to a Lamb wave.

9. Method according to claims 5 or 6, whereby a first scanning pulse is emitted for purposes of localization and checking structural integrity, then the antenna is orientated, and thirdly a new pulse is emitted for the purpose of evaluating the backscattered acoustic rays corresponding to a Lamb wave.

10. A device for locating and characterizing flaws in a known, submerged metal structure, wherein the following are provided:

an acoustic antenna comprising
means for supporting and keeping said antenna relatively stationary in the liquid medium,
a spherical transmitting source,
and a concentrically arranged spherical receiving surface, said latter surface being formed by x individual sensing cells carried on a structure which is transparent to back reflected acoustic radiation;

means for preprocessing the echo signals, comprising, for each sensor cell,
at least one preamplifier,
a filter associated with a logical comparator,
and a filtered-signal addressing and labelling module;

means for electronically transmitting the latter data;
and a central processing unit, including
a computer,
display means
and a mass storage.

11. Device according to claim 10, wherein said central processing unit further comprises preconfiguration synthesizing means for the receiving surface of said antenna.

* * * * *